United States Patent [19]
Duvel

[11] Patent Number: 5,945,093
[45] Date of Patent: Aug. 31, 1999

[54] CONDITIONING SHAMPOO

[75] Inventor: Lane A. Duvel, Rockford, Mich.

[73] Assignee: Amway Corporation, Ada, Mich.

[21] Appl. No.: 09/064,232

[22] Filed: Apr. 22, 1998

[51] Int. Cl.[6] .................................................. A61K 7/075
[52] U.S. Cl. .................................. 424/70.12; 424/70.11; 424/70.13
[58] Field of Search .............................. 424/70.11, 70.12, 424/70.13

[56] References Cited

U.S. PATENT DOCUMENTS

| | | | |
|---|---|---|---|
| 4,479,893 | 10/1984 | Hirota et al. .............................. | 252/542 |
| 4,976,956 | 12/1990 | Noe ....................................... | 424/70.12 |
| 5,034,218 | 7/1991 | Duvel et al. ........................... | 424/70.12 |
| 5,114,706 | 5/1992 | Duvel ................................... | 424/70.17 |
| 5,198,209 | 3/1993 | Zhou et al. ........................... | 424/70.122 |
| 5,211,883 | 5/1993 | Yamashina et al. .................... | 252/546 |
| 5,328,685 | 7/1994 | Janchitraponvej et al. ......... | 424/70.11 |
| 5,358,667 | 10/1994 | Bergmann ............................... | 252/547 |
| 5,714,135 | 2/1998 | Lee et al. .............................. | 424/70.11 |
| 5,744,147 | 4/1998 | Cauwet et al. .......................... | 424/401 |

*Primary Examiner*—Peter F. Kulkosky
*Attorney, Agent, or Firm*—Brinks Hofer Gilson & Lione

[57] ABSTRACT

An improved stable conditioning shampoo imparts improved physical and cosmetic properties to the hair such as wet and dry comb, wet and dry feel, gloss, static control and manageability, yet does not cause build-up and does not contain any polyhydric compounds. The shampoo includes an anionic surfactant, a water soluble cationic surfactant, a water-insoluble conditioning agent, and a suspending agent where the suspending agent is a mixture of a cellulose derivative and a PVM/MA Decadiene crosspolymer. The conditioning shampoo is stable for extended periods.

17 Claims, No Drawings

CONDITIONING SHAMPOO

The present invention relates to a conditioning shampoo composition and to its method of manufacture. In particular, the present invention is directed to a stable conditioning shampoo that includes water-insoluble conditioning agents but is free from polyhydric compounds. Advantageously, the composition remains stable after prolonged periods due to the presence of a suspending agent that is a combination of a cellulose derivative and a cross-linked copolymer.

BACKGROUND OF THE INVENTION

The formulation of conditioning shampoos has been difficult because of several reasons. One problem is that anionic surfactants, which are desired for their excellent cleaning ability, are incompatible with cationic surfactants, which are desired for their hair conditioning properties.

Another problem is that water-insoluble conditioning agents, such as silicone-containing compounds, which are added to provide a degree of softness and luster to the hair typically cause the composition to be unstable. A related problem is that it is difficult to keep these silicone-containing compounds suspended or maintained in a stable form while retaining the performance attributes desired from the conditioning shampoo. One solution to that problem has been proposed in U.S. Pat. No. 5,198,209 where a particular N-alkylated pyrolidone is suggested to be useful for maintaining the composition in a stable form. Unfortunately, the particular pyrolidone is not a suspending agent and it is has now been found that after a few days at elevated temperatures on the order of 40° C. to about 50° C., a white, creamy layer forms at the surface.

Another solution to that problem that has been proposed by Bergmann, U.S. Pat. Nos. 5,275,761, 5,358,667, and 5,456,863 is to use a polyhydric compound as an essential element to emulsify, add phase-stability, prevent anionic-cationic interaction and couple the insoluble conditioning agent with the cationic surfactant. The polyhydric is used with a carboxylated surfactant, a hydrophilic quaternary ammonium, or a fafty alkyl compound.

Surprisingly and unexpectedly, it has been found that a conditioning shampoo can be prepared that is substantially free of a polyhydric compound. In fact, when a polyhydric compound is added to the conditioning shampoo of the present invention the viscosity and foam volume were significantly reduced, with no increase in stability to off-set the negative impact on viscosity and foam volume.

SUMMARY OF THE INVENTION

The present invention provides a stable, homogeneous conditioning shampoo that cleanses the human hair and, at the same time, provides improved physical and cosmetic properties in a single application.

The conditioning shampoo composition comprises from about 5% to about 50% of an anionic surfactant, from about 0.1% to about 10% of a cationic surfactant, from about 0.1% to about 10% of a water insoluble conditioning agent selected from the group of a silicone-containing compositions, and from about 0.1% to about 5% of a suspending agent in a suitable carrier such as water and wherein the composition is free of a polyhydric compound.

All percentages referred to in the specification and appended claims are by weight unless otherwise stated.

DETAILED DESCRIPTION OF THE PREFERRED EMBODIMENTS

The conditioning shampoo composition comprises from about 5% to about 50% of an anionic surfactant, from about 0.1% to about 10% of a water soluble cationic surfactant, from about 0.1% to about 10% of a water insoluble conditioning agent selected from the group of a silicone-containing compositions and mixtures thereof; from about 0.1% to about 5% of a suspending agent in a suitable carrier such as water and wherein the composition is free of a polyhydric compound.

Surprisingly and unexpectedly, the conditioning shampoo composition of the present invention is stable over an extended period of time so that it resists phase separation of the water insoluble conditioning agent from the aqueous composition. The easy-to-apply composition effectively cleans the hair and imparts excellent wet and dry comb conditioning properties to the hair. In general, the cleansed hair demonstrates improved physical and cosmetic conditioning properties such as gloss, thickness, softness, manageability and body. As explained more fully below, it is surprising and unexpected for a composition that includes an anionic cleansing surfactant, a cationic conditioner, and a water-insoluble conditioning agent to exhibit such excellent composition stability in regard to phase separation and to cleanse the hair and impart such improved conditioning properties to the hair in a single application of the composition to the hair, all without the deleterious effects of a polyhydric compound.

The anionic cleansing surfactants useful in the present composition include those water soluble anionic surfactants known or previously used in the art of shampoos. The water soluble anionic surfactants are preferred because they effectively clean the hair and generate a high, stable foam level that many consumers equate with cleaning efficacy. Nonionic and amphoteric surfactants generally are not as effective in cleansing the hair and do not provide the high foam level desired by consumers. As a result, the nonionic and amphoteric surfactants are not desired as the primary cleansing surfactant in the compositions of the present invention. Nevertheless, they may be optionally included to help increase or stabilize the foam to provide a suitable composition viscosity, or to provide other functional or aesthetic properties to the composition.

Typically, the water soluble anionic cleansing surfactants include a hydrophobic moiety, such as a carbon chain including about 8 carbon atoms to about 30 carbon atoms, particularly from about 12 carbon atoms to about 20 carbon atoms, and a hydrophilic moiety such as sulfate, sulfonate, carbonate, phosphate or carboxylate. Often, the hydrophobic carbon chain is etherfied, such as with ethylene oxide or propylene oxide, to impart particular physical or reduced surface tension.

Suitable anionic surfactants include, but are not limited to, alkyl sulfates, alkyl ether sulfates, sulfate esters of an alkylphenoxy polyoxyethylene ethanol, alpha-olefin sulfonates, beta-alkoxy alkane sulfonates, alkyl arylsulfonates, alkyl carbonates, alkyl ether carboxylates, fatty acids, sulfosuccinates, alkyl ether sulfosuccinates, sarcosinates, fatty taurides, sulfated monoglycerides, fatty acid amido polyoxyethylene sulfates and isethionates, and mixtures thereof. Other suitable anionic surfactants are described in McCutcheon's Detergents and Surfactants, published by McCutcheon Division, MC Publishing Co., which is incorporated herein by reference.

Usually, the anionic surfactant is present in the composition as a neutralized salt in the form of a sodium, potassium, lithium, ammonium, alkylammonium, or hydroxyalkylammonium salt, wherein the alkyl moiety includes from 1 to about 3 carbon atoms. The alkyl sulfates and alkyl ether sulfates are particularly preferred. Examples of such sulfates include, but are not limited to, the ammonium, monoethanolamine, diethanolamine, triethanolamine, isopropylamine, sodium, potassium, lithium, or magnesium salts of lauryl sulfate, dodecylbenzenesulfonate, lauryl sulfosuccinate, lauryl ether sulfate, lauryl ether carboxylate, lauryl sacrosinate, cocomethyl tauride, and sulfosuccinate half ester amine, and mixtures thereof.

A preferred anionic is a mixture of an alkyl sulfate and an alkyl ether sulfate. In particular, a mixture of an ammonium lauryl sulfate and an ammonium lauryl ether sulfate (having an average of about 3 moles of ethylene oxide) is preferred. In this preferred embodiment, the ratio of alkyl sulfate to alkyl ether sulfate is from about 1:1 to about 10:1 more preferably from about 2:1 to about 6:1, and desirably from about 4:1 to about 5:1.

The anionic surfactant is present in an amount from about 5% to about 50% preferably from about 10% to about 30%, more preferably from about 10% to about 20%, and most preferably from about 14% to about 18%. It is believed that amounts greater than 50% do not enhance the cleanliness of the hair and is therefore wasted. In a preferred embodiment, the alkyl ether sulfate comprises from about 5% to about 50% of the total anionic surfactant, preferably from about 10% to about 35%, more preferably from about 15% to about 25% of the total anionic surfactant.

The composition includes a cationic surfactant, preferably a water soluble cationic surfactant. Useful water soluble cationic surfactants are described in McCutcheon's Detergents and Surfactants, published by McCutcheon Division, MC Publishing Co., which is incorporated herein by reference.

A preferred class of water-soluble cationic surfactants include acid neutralized amidoamine compounds. These compounds are compatible with anionic surfactants and can provide conditioning properties not seen in other formulations incorporating amidoamines specifically at these levels. The preferred amidoamine compounds have the general structural formula (I) or (II);

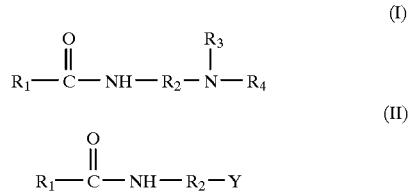

where $R_1$ is a fatty acid chain containing from about 11 to about 21 carbon atoms, $R_2$ is an alkyl group containing from about two to about four carbon atoms, $R_3$ is hydrogen, methyl, ethyl, a hydroxyalkylene group or a hydroxyalkyl group containing from about one to about three carbon atoms, $R_4$ is methyl, ethyl, hydroxyalkylene group or hydroxyalkyl group containing from about one to about three carbon atoms, and Y is a heterocyclic nitrogen-containing moiety, like morpholine.

An example of an amidoamine compound having the general structural formula (I) that can be used in the composition and method of the preferred embodiment is one where $R_1$ has 17 carbon atoms, $R_2$ has 2 carbon atoms, $R_3$ is hydrogen and $R_4$ is ethanol and is known as stearamidoethyl ethanolamine. Other suitable amidoamine compounds that can be used in the present invention include but are not limited to stearamidoethyl diethanolamine as well as those having either one or two hydroxymethyl, hydroxypropyl, methyl or ethyl moieties or combinations thereof, present on an amino nitrogen in place of the hydroxyethyl moieties. Examples of such amido amine compounds include but are not limited to, dimethylaminopropyl stearamide, diethylaminoethyl stearamide, and dimethylaminopropyl myristamide.

Examples of amidoamine compounds having the general structural formula (II) that can be used in the composition and method of the present invention include but are not limited to isostearamidopropylmorpholine and stearamidopropylmorpholine.

After neutralization with a suitable acid, the above described amidoamine compounds exhibit the properties of a cationic surfactant. In the free amine state, the amidoamine compounds are insoluble in water. After acid neutralization, however, they are water soluble. Accordingly, in the acid-neutralized state, they behave like a cationic surfactant and thus provide conditioning properties to human hair.

The acid used to neutralize the amidoamine compound can be any acid of sufficient strength to neutralize a free-amine nitrogen. Such acids include, but are not limited to, hydrochloric acid, sulfuric acid, nitric acid, phosphoric acid, lactic acid, citric acid, tartaric acid, acetic acid, gluconic acid, glycolic acid and propionic acid, or mixtures thereof. The amidoamine compound can be neutralized in situ or can be obtained commercially.

Preferably, the acid neutralized compound is obtained commercially as for example isostearamidopropyl morpholine lactate or stearamidopropyl dimethylamine lactate under the tradenames Incromate ISML and Incromate SDL, respectively.

The water soluble cationic surfactant is incorporated in the composition of the present invention in an amount from about 0.1% to about 10%, preferably from about 0.5% to about 3%, more preferably from about 0.5% to about 1.5%, most preferably from about 0.6% to about 0.8%.

The composition includes a water insoluble conditioning agent selected from the group of silicone-containing compositions and mixtures thereof. The silicone-containing compositions include the volatile and nonvolatile silicones, although the nonvolatile are preferred.

The nonvolatile silicones include, but are not limited to polyalkyl siloxanes, polyaryl siloxanes, and polyalkylaryl siloxanes and mixtures thereof. Preferably, the nonvolatile silicone is a polydimethylsiloxane that has a viscosity from about 5 to about 1,000,000 cs. These siloxanes are commercially available from Dow Corning Chemical Co. as, for example, the Dow Corning 200 Series. Preferably, the viscosity ranges from about 500 to about 600,000 cs. The polydimethylsiloxanes can be linear or branched and have the following general formula:

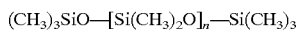

wherein n is a number from about 2,000 to about 15,000 and preferably from about 2,000 to about 7,000. Mixtures of a lower molecular weight polydimethylsiloxane and a higher molecular weight polydimethylsiloxane may also be used.

The nonvolatile polyalkylaryl siloxanes that may be used include, for example, polymethylphenylsiloxanes having viscosities of about 15 to about 65 cs. These siloxanes are commercially available from Dow Corning as Dow Corning 556 Cosmetic Grade Fluid.

As noted above, volatile silicones may be included in the present composition. Examples of useful volatile silicones include linear or cyclic low molecular weight polydimethylsiloxanes. It is believed that these volatile silicones provide lubrication and hair conditioning properties to we hair and have sufficient volatility to slowly volatilize from the hair so that a residual buildup of silicone compound is not present on the dry hair.

One example of a linear, low molecular weight volatile polydimethylsiloxane compound that can be used in the present composition is hexamethyldisiloxane, available commercially under the trade name Dow Corning 200 Fluid. It has a viscosity of 0.65 cs, is highly volatile, is non-greasy, provides lubrication, and improves the overall combing properties of the hair.

Examples of cyclic volatile polydimethylsiloxanes include but are not limited to the cyclomethicones such as octamethylcyclotetrasiloxane and decamethylcyclopentasiloxane.

The water-insoluble conditioning agent is added to the composition of the present invention in an amount sufficient to impart improved combing and improved feel, such as softness to the hair after shampooing. Accordingly, the water-insoluble conditioning agent is added in an amount from about 0.1% to about 10%, preferably from about 1% to about 5%, more preferably from about 1% to about 3%.

In a preferred embodiment the composition also includes from about 0.1% to about 2%, preferably from about 0.1% to about 1% of a water-insoluble, non-volatile amine-functional siloxane in addition to the other water-insoluble conditioning agents. A preferred amine-functional silicone for use is a trimethylsilylamodimethicone which has a viscosity from about 50 to about 500 cs. This is available from Dow Corning Chemical Co. as Dow Corning Q2-8220 or Dow Corning 929 Emulsion.

To ensure stability of the composition, a suspending agent is included. The suspending agent is a mixture of a cellulose derivative and a cross-linked copolymer, particularly a PVM/MA Decadiene crosspolymer (methyl vinyl ether/maleic anhydride copolymer cross linked with 1,9-decadiene). The suspending agent of the present invention will stabilize the composition of the present invention, which includes the water-insoluble conditioning agent, for up to 1 month at 50° C. and up to 3 months at 40° C., without any deleterious effects on the functional performance of the composition. Surprisingly, it has been found that when only one of the constituents of the suspending agent of the present invention is used, the composition is not stable and will separate.

Suitable cellulose derivatives include methylcellulose, hydroxybutyl methylcellulose, hydroxypropylcellulose, hydroxypropyl methylcellulose, hydroxyethyl ethylcellulose, and hydroxyethylcellulose. The PVM/MA Decadiene crosspolymer is available under the tradename STABILEZE® 06 and QM from ISP Chemicals.

The suspending agent is incorporated in the composition at a level of from about 0.1% to about 5%, preferably from about 0.3% to about 2.5%, more preferably from about 0.5% to about 1.5% and most preferably from about 0.8% to about 1.3%. The ratio of the cellulose derivative to cross polymer may be in the range from about 5:1 to about 1:5, preferably from about 2:1 to about 1:2.

The composition of the present invention is preferably an aqueous composition and therefore contains water in an amount from about 20% to about 90%, preferably from about 50% to about 80%.

The conditioning shampoo of the present invention may also contain a variety of nonessential optional ingredients suitable for making the compositions acceptable to consumers. Such optional cosmetic components and additives include, but are not limited to, nonionic surfactants, amphoteric surfactants, fragrances, dyes, hair colorants, opacifiers, pearlescing agents, dandruff control agents, foam stabilizers, preservatives, water softening agents, acids, alkalis, buffers and the like. These optional components and additives usually are present in weight percentages of 0% to less than about 5% by weight each, and usually about 0.1% to about 20% by weight of the composition in total so long as they do not negatively affect the stability and functional performance characteristics of the composition of the present invention.

For example, to improve consumer acceptance, enhanced shampoo mildness and aesthetics, an amphoteric surfactant may be included in the hair shampoo-conditioner in an amount of 0% to about 5% by weight of the composition. In general, any amphoteric surfactant can be included in the composition of the present invention so long as the stability, conditioning, and cleansing efficacy of the composition are not adversely affected. Suitable amphoteric surfactants that can be included in the present invention are exemplified by, but are not limited to, betaines, hydroxypropylsultaines and amine oxides, or combinations thereof. In particular, useful amphoteric surfactants include cocamidopropyl betaine, lauramidopropyl betaine, coco/oleamidopropyl betaine, coco betaine, oleyl betaine, cocamidopropyl hydroxysultaine, tallowamidopropyl hydroxysultaine and dihydroxyethyl tallow glycinate, or combinations thereof.

The conditioning shampoo compositions of the present invention also can include nonionic surfactants to help impart aesthetic, physical or cleansing properties to the composition. Likewise, the compositions can include other conditioning agents, inorganic salts, and similar materials to provide the composition with desirable aesthetic or physical properties.

Representative nonionic surfactants include esters of polyols or sugars; fatty acid alkanolamides; pyrrolidones and the condensation products of ethylene oxide and long chain amides. These nonionic surfactants, as well as numerous others not cited herein, are well known in the art and are fully described in the literature, such as McCutcheon's Detergents And Emulsifiers, which is incorporated herein by reference.

In particular, a nonionic alkanolamide can be included in the composition to provide foam stability. The alkanolamide can be included in an amount of 0% to about 5% by weight of the composition. Accordingly, suitable alkanolamides include, but are not limited to, those known in the art of hair care formulations, such as cocamide MEA, cocamide DEA, soyamide DEA, lauramide DEA, oleamide MIPA, stearamide MEA, myristamide MEA, lauramide MEA, capramide DEA, ricinoleamide DEA, myristamide DEA, stearamide EEA, oleylamide DEA, tallowamide DEA, lauramide MEA, tallowamide MEA, isostearamide DEA, isostearamide MEA, and combinations thereof.

The nonionic surfactants known as the N-alkylated-2-pyrrolidones may also be useful in the compositions of the present invention. The alkyl group may be straight or branched and may include from about 8 to about 16 carbon atoms. A particularly preferred, pyrrolidone is lauryl pyrrolidone that is commercially available under the trade name Surfadone LP-300 from ISP.

Preservatives such as benzyl alcohol, methyl paraben, propylparaben, imidazolidinyl urea, diazolidinyl urea, chloromethyl isothiazolinone and methyl isothiazolinone, phenoxyethanol, and DMDM hydantoin can be used. Pearlescent agents can also be incorporated in the present compositions. Examples include ethylene glycol stearate, ethylene glycol distearate, mica coated by titanium dioxide.

The pH of the composition can be adjusted by agents such as citric acid, succinic acid, sodium hydroxide, triethanolamine and other known pH and buffering agents so that the pH of the composition is slightly acidic, i.e., from about 5.0 to about 6.5, preferably about 5.5.

Other optional ingredients include perfumes or fragrances, lipids, dyes, sequestering agents such as tetra-sodium EDTA, antioxidants such as tocopherol, BHT, BHA, and UV absorbers such as benzophenones.

EXAMPLES

The following are illustrative examples of formulations and compositions according to this invention and it should be understood that they do not limit the scope of the invention.

TABLE 1

| Ingredient | amount (wt %) |
| --- | --- |
| Ammonium lauryl sulfate (28%) | 45.00 |
| Ammonium laureth sulfate (28%) | 10.00 |
| Disodium laureth sulfosuccinate (30%) | 3.00 |
| Isostearamidopropyl Morpholine Lactate (25%) | 3.00 |
| Lauryl pyrrolidone | 1.00 |
| Dimethicone | 2.00 |
| Trimethylsilyamodimethicone | 0.50 |
| Hydroxypropyl Methylcellulose | 0.60 |
| PVM/MA Decadiene crosspolymer | 0.50 |
| Miscellaneous optional ingredients | 2.16 |
| Water | 32.24 |
| TOTAL | 100.00 |

In a preferred embodiment of the present invention, the conditioning shampoo composition consists essentially of from about 10% to about 30% of an anionic surfactant that is a mixture of an alkyl sulfate and an alkyl ether sulfate, from about 0.5% to about 3% of a water soluble cationic surfactant that is an acid-neutralized amidoamine wherein the amidoamine selected from the group consisting of isostearamidoproplymorpholine, stearamidopropylmorpholine, and mixtures thereof, from about 1% to about 5% of a water insoluble silicone-containing conditioning agent that comprises a mixture of a nonvolatile silicone selected from the group consisting of polyalkyl siloxanes, polyalkylaryl siloxanes, and mixtures thereof, and an amine-functional siloxane; from about 1% to about 5% of a suspending agent that comprises a mixture of a cellulose derivative and a PVM/MA decadiene cross polymer.

The compositions of the present invention can be made by a single phase addition procedure in the following manner. Referring to Table 1, water is added to a mixing tank and heated to about 185° F. Hydroxypropyl methylcellulose is then slowly added to the water with mixing. The PVM/MA decadiene crosspolymer is then added and mixed until completely dispersed. Thereafter, a portion of the anionic surfactant is added (all of the ammonium laureth sulfate together with a similar amount of the ammonium lauryl sulfate) along with all other ingredients, except for any preservatives, fragrances, and dyes until dispersed. The remaining anionic surfactant (ammonium lauryl sulfate) is added and the mix cooled to about 115° F. at which point the all miscellaneous optional ingredients are added until well dispersed. Upon completion, the viscosity of the composition is from about 5,000 to about 40,000 cs., preferably from about 15,000 to about 30,000 cs., more preferably about 25,000 cs.

It should be understood that a wide range of changes and modifications can be made to the embodiments described above. It is therefore intended that the foregoing description illustrates rather than limits this invention, and that it is the following claims, including all equivalents, which define this invention.

What is claimed:

1. A stable conditioning shampoo composition comprising by weight:

a. from about 5% to about 50% of an anionic surfactant;

b. from about 0.1% to about 10% of a water soluble cationic surfactant that is an acid-neutralized amidoamine;

c. from about 0.1% to about 10% of a water insoluble conditioning agent selected from the group of a silicone-containing composition and mixtures thereof; and d. from about 0.1% to about 5% of a suspending agent comprising a mixture of a cellulose derivative and a PVM/MA decadiene cross polymer;

wherein the composition is free of a polyhydric compound, wherein said conditioning shampoo composition is stable over a period of time so that it resists phase separation of the water insoluble conditioning agent from the aqueous composition.

2. The shampoo composition of claim 1 wherein the anionic surfactant is selected from the group consisting of an alkyl sulfate, an alkyl ether sulfate, a sulfate ester of an alkylphenoxy polyoxyethylene ethanol, an alpha-olefin sulfonate, a beta-alkoxy alkane sulfonate, an alkyl aryl sulfonate, an alkyl carbonate, a sulfosuccinate, an alkyl ether sulfosuccinate, a sacristan, an octoxynol phosphate, a nonoxynol phosphate, a taurate, a fatty tauride, a sulfated monoglyceride, a fatty acid polyoxyethylene sulfate, an isethienate, and mixtures thereof.

3. The shampoo composition of claim 2 wherein the anionic surfactant is selected from the group consisting of alkyl sulfates, alkyl ether sulfates, and mixtures thereof.

4. The shampoo composition of claim 1 wherein the anionic surfactant is a long chain alkyl sulfate having the formula $ROSO_3M$ wherein R is an alkyl or alkenyl of about 10 to about 20 carbon atoms and M is a water-soluble cation.

5. The shampoo composition of claim 4 wherein the anionic surfactant comprises ammonium lauryl sulfate.

6. The shampoo composition of claim 4 wherein the anionic surfactant further includes a long chain alkyl ether sulfate having the formula $RO(C_2H_4O)_nSO_3M$ wherein R is an alkyl or alkenyl having from about 10 to about 20 carbon atoms, n is from 1 to 10, and M is a water soluble cation.

7. The shampoo composition of claim 5 wherein the anionic surfactant further comprises ammonium laureth sulfate.

8. The shampoo of claim 7 wherein the ratio of ammonium lauryl sulfate to ammonium laureth sulfate is from about 1:1 to about 10:1.

9. The shampoo composition of claim 1 wherein the water soluble cationic surfactant is an acid-neutralized amidoamine wherein the amidoamine has the general structural formula (I) or (II);

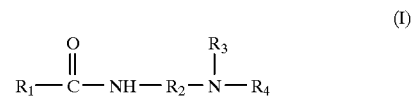

$$R_1-\overset{\overset{O}{\|}}{C}-NH-R_2-Y \qquad (II)$$

where $R_1$ is a fatty acid chain containing from about 11 to about 21 carbon atoms, $R_2$ is an alkyl group containing from about two to about four carbon atoms, $R_3$ is a hydrogen, methyl, ethyl or a hydroxyalkylene group containing from about one to about three carbon atoms, $R_4$ is methyl, ethyl or hydroxyalkylene group containing from about one to about three carbon atoms, and Y is a heterocyclic nitrogen-containing moiety, like morpholine.

10. The shampoo composition of claim 9 wherein the amidoamine is selected from the group consisting of stearamidoethyl ethanolamine, stearamidoethyl diethanolamine, dimethylaminopropyl stearamide, diethylaminoethyl stearamide, dimethylaminopropyl myristamide, isostearamidopropylmorpholine and stearamidopropylmorpholine, and mixtures thereof.

11. The shampoo composition of claim 10 wherein the amidoamine is pre-neutralized with lactic acid.

12. The shampoo composition of claim 1 wherein the water insoluble conditioning agent is a nonvolatile silicone selected from the group consisting of polyalkyl siloxanes, polyalkylaryl siloxanes and mixtures thereof.

13. The shampoo composition of claim 12 further comprising a non-volatile amine-functional siloxane.

14. The shampoo composition of claim 13 wherein the amine-functional siloxane is trimethylsilylamodimethicone.

15. The shampoo composition of claim 1 wherein the cellulose derivative is selected from the group consisting of methylcellulose, hydroxybutyl methylcellulose, hydroxypropylcellulose, hydroxypropyl methylcellulose, hydroxyethyl ethylcellulose, and hydroxyethylcellulose.

16. A stable conditioning shampoo composition comprising by weight:
    a. from about 5% to about 50% of an anionic surfactant, wherein the anionic surfactant is a mixture of a long chain alkyl sulfate having the formula $ROSO_3M$ wherein R is an alkyl or alkenyl of about 10 to about 20 carbon atoms and M is a water-soluble cation and a long chain alkyl ether sulfate having the formula $RO(C_2H_4O)_nSO_3M$ wherein R is an alkyl or alkenyl having from about 10 to about 20 carbon atoms, n is from 1 to 10, and M is a water soluble cation;
    b. from about 0.1% to about 10% of a water soluble cationic surfactant is an acid-neutralized amidoamine wherein the amidoamine has the general structural formula (I) or (II);

$$R_1-\overset{\overset{O}{\|}}{C}-NH-R_2-\overset{\overset{R_3}{|}}{N}-R_4 \qquad (I)$$

$$R_1-\overset{\overset{O}{\|}}{C}-NH-R_2-Y \qquad (II)$$

where $R_1$ is a fatty acid chain containing from about 11 to about 21 carbon atoms, $R_2$ is an alkyl group containing from about two to about four carbon atoms, $R_3$ is a hydrogen, methyl, ethyl or a hydroxyalkylene group containing from about one to about three carbon atoms, $R_4$ is methyl, ethyl or hydroxyalkylene group containing from about one to about three carbon atoms, and Y is a heterocyclic nitrogen-containing moiety, like morpholine.

c. from about 0.1% to about 10% of a water insoluble conditioning agent is a nonvolatile silicone selected from the group consisting of polyalkyl siloxanes, polyalkylaryl siloxanes, and mixtures thereof;
    d. from about 0.1% to about 5% of a suspending agent comprising a mixture of a cellulose derivative wherein the cellulose derivative is selected from the group consisting of methylcellulose, hydroxybutyl methylcellulose, hydroxypropylcellulose, hydroxypropyl methylcellulose, hydroxyethyl ethylcellulose, and hydroxyethylcellulose and a PVM/MA decadiene cross polymer;

wherein the composition is free of a polyhydric compound.

17. A stable conditioning shampoo composition by weight consisting essentially of:
    a. from about 5% to about 50% of an anionic surfactant that is a mixture of an alkyl sulfate and an alkyl ether sulfate;
    b. from about 0.1% to about 10% of a water soluble cationic surfactant that is an acid-neutralized amidoamine wherein the amidoamine is selected from the group consisting of isostearamidopropylmorpholine, stearamidopropylmorpholine, and mixtures thereof;
    c. from about 0.1% to about 10% of a water insoluble silicone containing conditioning agent that comprises a mixture of a nonvolatile silicone selected from the group consisting of polyalkyl siloxanes, polyalkylaryl siloxanes, and mixtures thereof, and an amine-functional siloxane; and
    d. from about 0.1% to about 10% of a suspending agent comprising a mixture of a cellulose derivative and a PVM/MA decadiene cross polymer;

wherein the composition is free of a polyhydric compound.

* * * * *

UNITED STATES PATENT AND TRADEMARK OFFICE
CERTIFICATE OF CORRECTION

PATENT NO.   : 5,945,093
DATED        : August 31, 1999
INVENTOR(S)  : Lane A. Duvel It is certified that error appears in the above-identified patent and that said Letters Patent is hereby corrected as shown below:

Title Page, Column 1,
Before line, under "U.S. DOCUMENTS", please insert the following:
-- 3,503,895   03/1970   Whelan
   3,950,260   04/1976   Eldib
   3,969,500   07/1976   Kennerley
   3,980,769   09/1976   Ghilardi et al.
   4,022,731   05/1977   Schmitt
   4,228,048   10/1980   Tesdahl
   4,260,528   04/1981   Fox et al.
   4,284,534   08/1981   Ehrlich
   4,414,144   11/1983   Liebowitz et al.
   4,434,087   02/1984   Hampson et al.
   4,472,297   09/1984   Bolich, Jr. et al. --.

After line 1, under "U.S. DOCUMENTS", please insert the following:
-- 4,576,744   03/1986   Edwards et al.
   4,654,207   03/1987   Preston
   4,704,272   11/1987   Oh et al.
   4,788,006   11/1988   Bolich, Jr. et al.
   4,897,262   01/1990   Nandagiri et al.
   4,954,336   09/1990   Chuang et al. --.

After line 2, under "U.S. DOCUMENTS", please insert the following:
-- 4,983,383   01/1991   Maksimoski et al. --.

After line 3, under "U.S. DOCUMENTS", please insert the following:
-- 5,106,609   04/1992   Bolich, Jr. et al. --.

After line 4, under "U.S. DOCUMENTS", please insert the following:
-- 5,151,209   09/1992   McCall et al.
   5,160,730   11/1992   Dubief et al.
   5,173,290   12/1992   Halloran et al.
   5,176,898   01/1993   Goldberg et al. --.

UNITED STATES PATENT AND TRADEMARK OFFICE
CERTIFICATE OF CORRECTION

PATENT NO.  : 5,945,093
DATED       : August 31, 1999
INVENTOR(S) : Lane A. Duvel It is certified that error appears in the above-identified patent and that said Letters Patent is hereby corrected as shown below:

Column 2,
After line 2, please insert the following:

| | | | |
|---|---|---|---|
| -- | 5,275,761 | 01/1994 | Bergmann |
|    | 5,277,899 | 01/1994 | McCall --. |

After line 4, please insert the following:

| | | | |
|---|---|---|---|
| -- | 5,380,528 | 01/1995 | Alban et al. |
|    | 5,409,695 | 04/1995 | Abrutyn et al. |
|    | 5,420,118 | 05/1995 | Alban et al. |
|    | 5,456,863 | 10/1995 | Bergmann |
|    | 5,482,703 | 01/1996 | Pings |
|    | 5,567,426 | 10/1996 | Nadaud et al. |
|    | 5,573,709 | 11/1996 | Wells |
|    | 5,599,800 | 02/1997 | Candau et al. --. |

After line 6, please insert a new item as follows:

-- FOREIGN PATENT DOCUMENTS

| | | | | | |
|---|---|---|---|---|---|
| 0 | 013 | 836 | A1 | 08/1980 | Europe |
| 0 | 051 | 983 | A1 | 05/1982 | Europe |
| 0 | 071 | 413 | A2 | 02/1983 | Europe |
| 0 | 071 | 414 | A2 | 03/1983 | Europe |
| 0 | 089 | 213 | A2 | 09/1983 | Europe |
| 0 | 463 | 780 | B1 | 01/1992 | Europe |
| 0 | 529 | 883 | B1 | 03/1993 | Europe |
| 1,054,244 | | | | 01/1967 | United Kingdom |
| 1,071,660 | | | | 06/1967 | United Kingdom |
| 1,073,655 | | | | 06/1967 | United Kingdom |
| 1,250,614 | | | | 10/1971 | United Kingdom |
| 1,270,040 | | | | 04/1972 | United Kingdom |
| 1,380,402 | | | | 01/1975 | United Kingdom |
| 1,429,639 | | | | 03/1976 | United Kingdom |
| 1,460,893 | | | | 01/1977 | United Kingdom |
| 1,471,406 | | | | 04/1977 | United Kingdom |
| 1,512,355 | | | | 06/1978 | United Kingdom |
| 1,576,946 | | | | 10/1980 | United Kingdom |
| 1,584,127 | | | | 02/1981 | United Kingdom |

UNITED STATES PATENT AND TRADEMARK OFFICE
CERTIFICATE OF CORRECTION

PATENT NO.   : 5,945,093
DATED        : August 31, 1999
INVENTOR(S)  : Lane A. Duvel Page 3 of 3

It is certified that error appears in the above-identified patent and that said Letters Patent is hereby corrected as shown below:

GB   2   095   276   A   09/1982   United Kingdom
    GB   2   103   236   A   02/1983   United Kingdom
    GB   2   104   913   A   03/1983   United Kingdom
    GB   2   105   325   A   03/1983   United Kingdom
    GB   2   108   520   A   05/1983   United Kingdom
    GB   2   126   243   A   03/1984   United Kingdom
    GB   2   130   236   A   05/1984   United Kingdom --.

Signed and Sealed this

Thirtieth Day of October, 2001

Attest:

NICHOLAS P. GODICI
Attesting Officer     Acting Director of the United States Patent and Trademark Office